United States Patent [19]

Jacobs et al.

[11] Patent Number: 4,849,410
[45] Date of Patent: Jul. 18, 1989

[54] PSEUDOPTEROSIN AND SYNTHETIC DERIVATIVES THEREOF

[75] Inventors: Robert S. Jacobs, Santa Barbara; William H. Fenical, San Diego, both of Calif.

[73] Assignee: The Regents of the University of California, Alameda, Calif.

[21] Appl. No.: 85,628

[22] Filed: Aug. 14, 1987

Related U.S. Application Data

[63] Continuation-in-part of Ser. No. 723,214, Apr. 15, 1982, Pat. No. 4,745,104.

[51] Int. Cl.$^4$ ............... A61K 31/70; C07H 15/24
[52] U.S. Cl. ................................ 514/33; 536/18.1
[58] Field of Search ........................ 514/33; 536/18.1

[56] References Cited

U.S. PATENT DOCUMENTS 4,447,445  5/1984  Manoalide .................... 424/279
4,521,592  6/1985  Dahmen et al. ................ 536/9.1

OTHER PUBLICATIONS

Johnson et al., Cancer Treatment Reviews (1975), vol. 2, pp. 1–31.
Look, S. A., Studies of the Natural Products Chemistry of Selected Carribean Gorgonians, Ph.D. Dissertation, University of California (1983).

*Primary Examiner*—Johnnie R. Brown
*Assistant Examiner*—Elli Peselev
*Attorney, Agent, or Firm*—Poms, Smith, Lande & Rose

[57] ABSTRACT

Methods for treating mammals to reduce pain, reduce cell proliferation and/or reduce inflammation are described based on administering to the mammals compounds having the formula

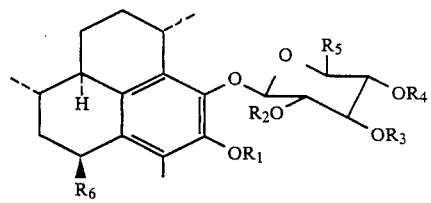

wherein $R_1$, $R_2$, $R_3$ and $R_4$ are hydrogen or an acyl group having from 1 to 6 carbon atoms; $R_5$ is hydrogen, $CH_3$ or $CH_2OH$ and $R_6$ is a hydrocarbon having from 1 to 10 carbon atoms. Natural and synthetic 1,12-seco derivatives with similar utilities are disclosed. Natural and synthetic derivatives are also disclosed where the sugar moiety is attached at the C-10 carbon on the tricyclic diterpene moiety instead of the C-9 carbon.

10 Claims, No Drawings

PSEUDOPTEROSIN AND SYNTHETIC DERIVATIVES THEREOF

BACKGROUND OF THE INVENTION

This application is a continuation-in-part of copending U.S. patent application Ser. No. 06/723,214 which was filed on Apr. 15, 1985, now U.S. Pat. No. 4,745,104.

The present invention relates generally to compounds having anti-inflammatory, anti-proliferative and analgesic activity and methods for using these compounds to reduce inflammation, cell proliferation and pain in mammals. More specifically, the present invention relates to natural and synthetic tricarbocyclic diterpene glycosides and their seco analogs which have been found to have anti-inflammatory, anti-proliferative and analgesic activity when administered to mammals.

This invention was made with Government support under Grant No: 80-AA-D-00120 with the National Oceanic & Atmospheric Administration to the University of California. The Government has certain rights in this invention.

Caribbean gorgonians (O. Gorgonacea, Ph. Cnidaria) are a diverse group of marine animals which are commonly known as sea whips and sea fans. A wide variety of Caribbean gorgonians are found in abundance in the shallow-water reefs of the West Indian region. A few of the Caribbean gorgonians have been analyzed for their chemical content and found to be a source of many diverse organic substances such as steroids, prostaglandins, lactones, sesquiterpenoid derivatives and diterpenoid metabolites. Some of these substances have been found to be biologically active.

Since only a small percentage of the total number of Caribbean gorgonian species have been examined for natural chemical products, there has been a continuing effort by a number of researchers to examine additional gorgonian species in order to isolate possible novel natural chemical compounds.

Recently, a number of selected Caribbean gorgonians were studied in depth to isolate and identify natural chemical products (Look, S. A., Studies of the Natural Products Chemistry of Selected Caribbean Gorgonians, Ph.D. Dissertation, University of California, 1983). The contents of the dissertation published in connection with this study are hereby incorporated by reference. Numerous novel chemicals were isolated and identified during this study. One of the novel natural chemical compounds isolated during the study was Pseudopterosin A. Pseudopterosin A is a tricarbocyclic diterpene glycoside having the chemical structure

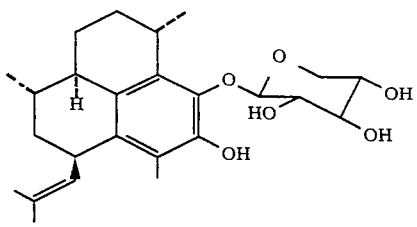

SUMMARY OF THE INVENTION

The present invention is based on the discovery that Pseudopterosin A and certain natural and synthetic derivatives of Pseudopterosin A, along with their secoanalogs, are effective as: anti-inflammatory agents; anti-proliferative agents; and analgesic agents.

One feature of the present invention involves a method for treating mammals suffering from pain to reduce pain which comprises administering to the mammal a pain reducing effective amount of a composition consisting essentially of a compound having the structure

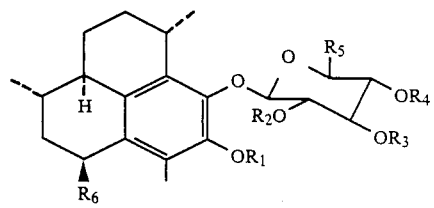

wherein $R_1$, $R_2$, $R_3$ and $R_4$ are hydrogen or an acyl group having from to to 6 carbon atoms, $R_5$ is hydrogen, $CH_3$ or $CH_2OH$, and $R_6$ is a hydrocarbon having from 1 to 10 carbon atoms; and a pharmaceutically acceptable carrier compound therefor.

Another feature of the present invention involves a method for treating mammals to reduce inflammation comprising the step of administering a compound as set forth in the preceding paragraph to the mammal in an inflammation reducing effective amount. A further feature involves the use of the compounds defined in the preceding paragraph in a method for treating mammals to reduce the proliferation of proliferating cells in lymphoma type cancers, such as leukemia or Hodgkins disease.

The present invention also includes a new group of synthetic compounds which are useful in the above methods and which are synthetic derivatives of pseudopterosin. These synthetic compounds have the generalized structure

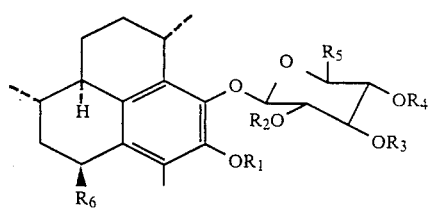

wherein $R_1$, $R_2$, $R_3$ and $R_4$ are hydrogen or an acyl group having from 1 to 6 carbon atoms; $R_5$ is hydrogen, $CH_3$ or $CH_2OH$ and $R_6$ is a hydrocarbon having from 1 to 10 carbon atoms; and wherein if $R_6$ is 2-methyl-1-propene, then $R_5$ is $CH_2OH$ or if $R_6$ is 2-methyl-1-propene and $R_5$ is hydrogen, then three or less of said $R_1$, $R_2$, $R_3$ or $R_4$ are hydrogen and if one of $R_1$, $R_2$, $R_3$ or $R_4$ is acetate, then two or less of said $R_1$, $R_2$, $R_3$ or $R_4$ are hydrogen.

The present invention also includes pharmaceutical compositions for use as anti-inflammatory agents, anti-proliferative agents and/or analgesic agents which consist essentially of an effective amount of one or more of the above defined synthetic compounds and a pharmaceutically acceptable carrier.

Also included are compounds having the structure

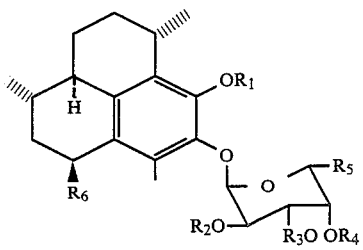

wherein $R_1$, $R_2$, $R_3$ and $R_4$ are hydrogen or an acyl residue (—COR) having from 1 to 6 carbon atoms; $R_5$ is hydrogen, $CH_3$ or $CH_2OH$ and $R_6$ is a hydrocarbon having from 1 to 10 carbon atoms.

The above compounds are similar to Pseudopterosin A and its derivative compounds except that the sugar moiety is attached at the 10 carbon on the tricyclic diterpene moiety rather than at the 9 carbon. These compounds have been found to also be effective as antiinflammatory and analgesic agents. They are also expected to be effective anti-proliferative agents for use in treating lymphoma type cancers.

The above discussed and many other features and attendant advantages of the present invention will become apparent as the invention becomes better understood by reference to the following detailed description.

DETAILED DESCRIPTION OF THE INVENTION

The compounds of the present invention fall into four basic groups: (1) naturally occurring Pseudopterosin A and the naturally occurring derivatives of Pseudopterosin A which have been isolated from Caribbean gorgonians of the genus Pseudopterogorgia; (2) synthetic derivatives of Pseudopterosin A; (3) the bicyclic derivatives or seco-analogs of the natural and synthetic pseudopterosin compounds of groups (1) and (2); and (4) Pseudopterosin A related compounds wherein the sugar moiety is attached at the C-10 position on the diterpene ring instead of the C-9 position.

The generalized structure for pseudopterosin compounds belonging to groups (1) and (2) above is

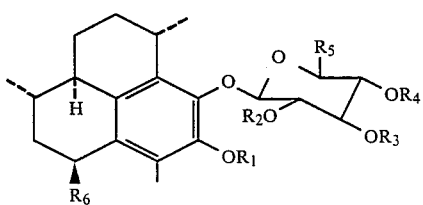

wherein $R_1$, $R_2$, $R_3$ and $R_4$ are hydrogen or an acyl group having from 1 to 6 carbon atoms, $R_5$ is hydrogen, $CH_3$ or $CH_2OH$ and $R_6$ is a hydrocarbon having from 1 to 10 carbon atoms.

Naturally occurring pseudopterosin compounds which were isolated from Caribbean gorgonia according to the dissertation of S. A. Look were those where:

Compound I—$R_1$, $R_2$, $R_3$ and $R_4$=H; $R_5$=H; and $R_6$=2-methyl-1-propene(pseudopterosin A)

Compound II—$R_1$, $R_2$, $R_4$=H; $R_3$=Acetate; $R_5$=H; and $R_6$=2-methyl-1-propene Compound III—$R_1$, $R_3$, $R_4$=H; $R_2$=Acetate; $R_5$=H; and $R_6$=2-methyl-1-propene All of the above described pseudopterosin natural products can be isolated and purified by the same chemical methods. An exemplary isolation of Compounds I–III involves stripping freshly collected Pseudopterogorgia species of lateral branchlets and storing the combined branchlets in the frozen state. The defrosted animals are ground in warm 10% methanol in chloroform and the insoluble tissues are filtered. The filter cake is re-extracted twice with the same solvent. The extracts are combined and the solvents are removed by evaporation at reduced pressure and at a temperature under 40° C. The residual tar is dissolved in chloroform, dried by the addition of liberal quantities of anhydrous magnesium sulfate, the magnesium sulfate is filtered, and the solvent is once again removed at reduced pressure. The yield of residual "crude extract" is generally between 6 and 9% of the dry weight of the animal tissue.

The various naturally occurring pseudopterosin compounds are isolated from the "crude extract" by a series of sequential silica gel chromatographic techniques. Approximately 30 grams of extract is dissolved in isooctane and applied to a column (10×6 cm) of TLC-grade silica gel made in a sintered-glass vacuum funnel. The chromatography is conducted with solvent mixtures beginning with 100% isooctane and ending with 100% ethyl acetate. The process creates 12–15 "fractions" which contain various percentages of pseudopterosin derivatives. The final purification of the natural products is accomplished by high-performance liquid chromatography on 1.3×50 cm silica gel columns with appropriate isooctane-ethyl acetate mixtures.

In most cases pseudopterosins are isolated as viscous oils or amorphous solids, but in one case (Compound II), the derivative was crystalline. Additional details of isolation and purification of pseudopterosin and its naturally occurring derivatives are set forth in the published dissertation of S. A. Look which has been previously incorporated by reference.

Synthetic derivatives of the naturally occurring pseudopterosin compounds include compounds according to the above general structure in which if $R_6$ is 2-methyl-1-propene, then $R_5$ is $CH_2OH$, or if $R_6$ is 2-methyl-1-propene and $R_5$ is hydrogen, then three or less of said $R_1$, $R_2$, $R_3$ or $R_4$ are hydrogen, and if one of $R_1$, $R_2$, $R_3$ or $R_4$ is acetate, then two or less of said $R_1$, $R_2$, $R_3$ or $R_4$ are hydrogen.

Exemplary groups which may be attached at the $R_1$, $R_2$, $R_3$ or $R_4$ position in addition to acetate are simple acyl derivatives having from 1 to 6 carbon atoms. Exemplary groups which may be attached at the R, position are alcohols, aldehydes, epoxides, ketones, acids, or other solubility-modifying groups as part of an alkyl residue from 4 to 10 carbon atoms.

Hydrogen is substituted at position $R_5$ when a pentose sugar moiety is desired with $R_5$ being $CH_2OH$ when a hexose moiety is desired.

Specific exemplary synthetic pseudopterosin compounds include:

Compound IV—$R_1$, $R_2$, $R_3$, $R_4$=Acetate; $R_5$=H; and $R_6$=2-methyl-1-propene.

Compound V—$R_1$, $R_2$, $R_3$, $R_4$=hydrogen; $R_5$=H; and $R_6$=2-methyl-1-propenemoxide;

Compound VI—$R_1$, $R_2$, $R_3$, $R_4$=hydrogen; $R_5$=H; and $R_6$=1-keto-2-methylpropane Compound VII—$R_1$, $R_2$, $R_3$, $R_4$=H; $R_5$=H; and $R_6$=2-methylpropane The procedures for substituting the wide variety of R groups into the pseudopterosin compound are conventional in nature and involve substitution of the $R_1$-$R_4$ group either on a pentose ($R_5$=hydrogen) or hexose ($R_5$=$CH_3$ or $CH_2OH$) sugar component or the $R_6$ group on the tricarbocyclic diterpene structure.

Exemplary synthesis of the selected synthetic derivatives is as follows:

Compound IV—Pseudopterosin (29 mg, 0.067 mM) was dissolved in 2 ml dry pyridine and excess acetic anhydride (ca. 1 ml) was added with stirring at room temperature. After 24 hours, 10 ml dichlormethane was added and the organic phase was subsequently washed with 1 N hydrochloric acid, 5% sodium bicarbonate and saturated brine solutions. The organic phase was dried over anhydrous magnesium sulfate, and the solvent was removed under reduced pressure to yield the tetraacetate derivative IV (32 mg, 79%) as a mobile oil. Successful acetylation and the full assignment of this derivative was accomplished by combined spectral techniques.

Compound V—Pseudopterosin (97 mg, 0.22 mm) was dissolved in 5 ml methylene chloride at room temperature. Metachloroperbenzoic acid (MCPBA) (49.2 mg, 0.26 mM), buffered with sodium biphosphate, was dissolved all at once, the solution was stirred for 22 hours, and next excess aq. sodium bisulfite was added. The organic phase was extracted first with saturated sodium bicarbonante solution, then with brine and finally dried over anhydrous magnesium sulfate. Removal of solvent after filtering left 97.2 mg (97%) of a viscous oil identified as the corresponding epoxide on the basis of complete structural analysis involving spectral methods.

Compound VI—Compound V (21.3 mg, 0.048 mM) in 3 ml anhydrous diethyl ether was treated with 0.2 ml boron trifluoride etherate (Aldrich Chem. Co.) at 0°. The solution was stirred for 20 min, 5 ml distilled water was added, and the organic phase was increased by the addition of an additional 5 ml ether. The ether layer was washed with 5% sodium bicarbonate, dried over anhydrous magnesium sulfate and reduced in vacuo. The crude product was purified by silica gel HPLC to yield the ketone derivative (13 mg, 61%) as a colorless viscous oil.

Compound VII—Pseudopterosin A (58 mg, 0.13 mM) was combined with 5 ml ethyl acetate and a catalytic amount (ca. 20 mg) of 10% Palladium on carbon and the sealed flask was purged with hydrogen. The reaction was allowed to proceed for 72 hours and the catalyst was filtered. Removal of solvent at reduced pressure gave the dihydro product (32.7 mg, 56%) as a viscous oil which was sufficiently pure for further investigation on the basis of NMR analysis.

The bicyclic derivatives or seco analogs of the previously defined pseudopterosin compounds have the structure:

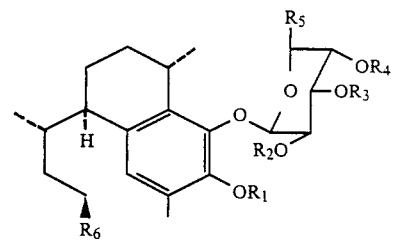

These derivatives or analogs are the same as the previous compounds except that they are the 1,12-seco analogs of the corresponding pseudopterosin compounds and they contain alpha linked sugars. The various R groups listed in the formula have the same definition as the R groups for the pseudopterosin compound as previously discussed.

Exemplary natural seco analogs of pseudopterosin are:

Compound VIII—$R_1$, $R_2$, $R_3$=H, $R_4$=Acetate; $R_5$=H; and $R_6$=2-methyl-1-propene.

Compound IX—$R_1$, $R_2$, $R_3$, $R_4$=H; $R_5$=H; and $R_6$=2-methyl-1-propene.

Compound X—$R_1$, $R_2$, $R_4$=H; $R_3$=Acetate; $R_5$=H; and $R_6$=2-methyl-1-propene The above naturally occurring seco analogs of pseudopterosin are isolated from Caribbean gorgonians in the same manner as pseudopterosin. Details of an exemplary procedure are set forth in the dissertation of S.A. Look which has been previously referenced.

Preparation of 1,12-seco analog derivatives corresponding to the synthetic derivatives of pseudopterosin may be carried out by the same methods defined in detail for pseudopterosin.

The fourth group of compounds are the same as the compounds in groups (1) and (2) discussed above except that the sugar moiety is linked as an alpha glycoside to the diterpene moiety at the C-10 hydroxyl group rather than at the C-9 hydroxyl. This additional group of compounds has the structure

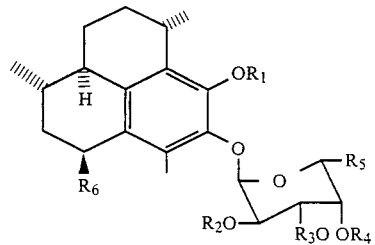

wherein $R_1$, $R_2$, $R_3$ and $R_4$ are hydrogen or an acyl group having from 1 to 6 carbon atoms, $R_5$ is hydrogen, $CH_3$ or $CH_2OH$, and $R_6$ is a hydrocarbon having from 1 to 10 carbon atoms.

We discovered that two additional naturally occurring pseudopterosin compounds were also present in Caribbean gorgonians wherein the sugar group is attached at the C-10 hydroxyl group. These newly isolated naturally occurring pseudopterosin type compounds have the structures set forth as XIV and XV below.

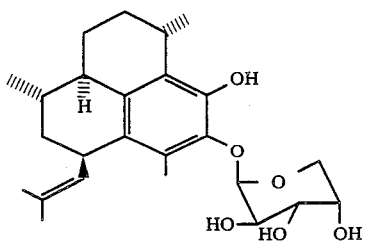

XIV

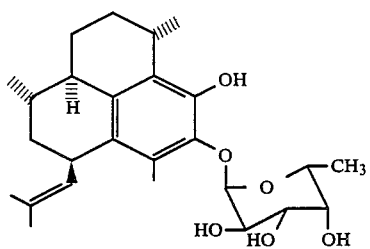

XV

Compounds XIV and XV were isolated from Pseudopterogorgia by the same basic extraction and separation procedure disclosed previously. This type of separation procedure is also disclosed in: (1) The pseudopterosins : Anti-inflammatory and analgesic natural products from sea whip *Pseudopterogorgia elisabethae,* Sally A. Look et al., Proc. Natl. Acad. Sci. U.S.A., Vol. 83, pp. 6238-6240, September 1986; and (2) The Pseudopterosins : A new class of Anti-inflammatory and Analgesic Diterpene Pentosides from the Marine Sea Whip *Pseudopterogorgia elisabethae* (Octocorallia), Sally A. Look et al., Journal of Organic Chemistry, 1986, 51, 5140.

The procedure for isolating Compounds XIV and XV involved preparing crude extracts of *Pseudopterogorgia elisabethae* by exhaustive extraction of the freeze dried animal with 10% methanol in chloroform. The condensed crude extract was fractionated over TLC grade silica gel (Merck) using rapid elution methods. Compounds I-III and a fourth compound having $R_1$, $R_2$, $R_3$ and $R_5$=H and $R_4$=Acetate (Compound IIA) were isolated by elution with varying quantities of ethyl acetate in methylene chloride. Compounds II and IIA were eluted with 10-30% ethyl acetate, while Compound III was isolated with 65% solvent mixture. Compound I was isolated by elution with 100% ethyl acetate.

Final elution of the column with 10% methanol in ethyl acetate yielded a complex fraction consisting of roughly an equimolar mixture of Compounds XIV and XV. This mixture was separated by preparative high performance liquid chromatography on silica gel (Whatman Magnum 9 Column) eluting with 5-7% methanol in diethyl ether. Under these conditions, Compound XV eluted just prior to the more polar Compound XIV.

Compounds XV and XIV are naturally occuring compounds within the fourth group of compounds that have been isolated. Synthetic derivatives of Compounds XIV and XV can also be made according to the same procedures used for preparing the synthetic derivatives of Pseudopterosin A. Exemplary synthetic derivatives of Compounds XIV and XV include:

Compound XVI—$R_1$, $R_2$, $R_3$, $R_4$=Acetate; $R_5$=H; and $R_6$=2-methyl-1-propene;

Compound XVII—$R_1$, $R_2$, $R_3$, $R_4$=hydrogen; $R_5$=H; and $R_6$=2-methyl-1-propeneoxide;

Compound XVIII—$R_1$, $R_2$, $R_3$, $R_4$=hydrogen; $R_5$=H; and $R_6$=1-keto-2-methylpropane; and Compound XIX—$R_1$, $R_2$, $R_3$, $R_4$=H; $R_5$=H; and $R_6$=2-methylpropane.

The procedures for substituting the wide variety of R groups into Compounds XIV and XV are conventional in nature and involve substitution of the $R_1$-$R_4$ group either on a pentose ($R_5$=hydrogen) or hexose ($R_5$=$CH_3$ or $CH_2OH$) sugar or the $R_6$ group on the tri-carbocyclic diterpene structure.

The linkage of the sugar moiety to the tricyclic diterpene moiety can be either an axial ($\alpha$) or an equatorial ($\beta$) glycoside linkage. The axial and equatorial glycoside linkages are possible in all of the compounds previously described including those with the sugar moiety attached at either the C-9 or C-10 carbon on the diterpene moiety. Deoxy pentose and hexose derivatives of these compounds and amino sugar derivatives are also contemplated.

The compounds of the present invention have been found to be effective anti-inflammatory agents, antiproliferative agents and analgesic agents for use in treating mammals. Examples demonstrating the effectiveness of selected representative exemplary compounds are set forth below.

Exemplary compounds I-X were tested according to the following well known pharmacological methods:

a. Mouse Ear Anti-Inflammatory Assay

Test compound and phorbol myristate acetate (PMA) are topically applied simultaneously to the pinnae of the ears of mice. Three hours twenty minutes after application, mice are sacrificed, ears removed and standard sized bores taken. Edema (inflammation) is measured as the difference in weight between control and treated ears.

b. Sperm Motility Assay

Male sea urchins are induced to spawn by injection of 0.5M KCl into the coelomic cavity. Sperm is collected via a pasteur pipette and stored in a test tube on ice. One drop of undiluted sperm is added to 25 ml of filtered fresh seawater, then 1.0 ml volumes of this solution are immediately added to test tubes containing 10 microliter test solution. Aliquots of sperm from each tube are observed microscopically for motility at a time two minutes after addition of sperm to test solution.

c. Fertilized Sea Urchin Egg Inhibition of Cleavage Assay for Anti-proliferation Sea urchins are induced to spawn by injection of 0.5M KCl into the coelomic cavity. Test compound is added to a 1% slurry of eggs within 5 minutes following fertilization and incubated until the completion of the division in control slurry, 90-120 minutes. Inhibition is measured as the present of undivided cells in the slurry at the end of this incubation.

d. Phenylquinone Assay for Analgesia

Test compound is injected subcutaneously into mice. After 30 minutes, phenylquinone is injected intraperitoneally to cause pain as indicated by writhing. Absence of or a statistically significant decrease in writhing is considered evidence of analgesia [Hendershot, L. C. and G. Forsaith, Pharmacol. Exp. Ther. 125, 237 (1959)].

The results of the pharmacological testing are set forth in the following Tables I-VI.

TABLE I

Effect of Pseudopterosin A (Compound I) on Phorbol Myristate Acetate (PMA) Induced Topical Inflammation of the Mouse Ear

| Treatment | Dose ug/ear | N | Ear Weight Mean ± S.E.M. |
|---|---|---|---|
| PMA alone | 1.5 | 24 | 20.83 ± 0.73 mg |
| PMA (1.5 ug) + Pseudopterosin A | 6.25 | 8 | 16.78 ± 0.91 mg** |
|  | 12.5 | 24 | 14.99 ± 0.6 mg* |
|  | 25.0 | 24 | 13.18 ± 0.53 mg* |
|  | 50.0 | 24 | 12.47 ± 0.46 mg* |
|  | 100.0 | 16 | 11.70 ± 0.37 mg* |

*Statistically significant difference, $p < .01$, Student's t-test
**Statistically significant difference, $p < .05$, Student's t-test

TABLE II

Effect of Pseudopterosin A (Compound I) on Arachidonic Acid (A.A.) Induced Topical Inflammation of the Mouse Ear

| Treatment | Dose ug/ear | N | Ear Weight Mean ± S.E.M. |
|---|---|---|---|
| A.A. alone | 25.0 | 8 | 16.37 ± 1.10 mg |
| A.A. (25.0 ug) + Pseudopterosin A | 50.0 | 8 | 13.33 ± 0.38 mg** |

**Statistically significant difference, $p < 0.05$, Student's t-test

TABLE III

Analgesic Activity of Pseudopterosin A (Compound I) Against Intraperitoneally Administered Phenylquinone (2.0 mg/kg)

| Treatment | Dose mg/kg | No. Animals | Mean No. Responses ± S.E.M. |
|---|---|---|---|
| Vehicle Control | — | 13 | 17.18 ± 0.90 |
| Pseudopterosin A | 3.1 | 9 | 8.55 ± 1.38* |
| Pseudopterosin A | 6.3 | 13 | 5.87 ± 1.24* |
| Pseudopterosin A | 12.5 | 13 | 5.87 ± 0.77* |
| Pseudopterosin A | 25.0 | 13 | 1.80 ± 1.31* |
| Pseudopterosin A | 50.0 | 5 | 0* |

*Statistically significant difference ($p < 0.001$) between control and each treated group. Student's t-test.

TABLE IV

Effects of Derivatives of Pseudopterosin on Phorbol Myristate Acetate Induced Topical Inflammation of the Mouse Ear

| Compound | Dose ug/ear | N | Mean Ear Weight ± S.E. |
|---|---|---|---|
| Pseudopterosin A Glycosides | | | |
| Acetone only | — | 16 | 11.25 ± 0.81 |
| PMA alone | 1.5 | 16 | 20.18 ± 4.29 |
| Compound II | 25.0 | 16 | 14.78 ± 2.79** |
|  | 50.0 | 16 | 14.31 ± 2.40** |
| Compound III | 25.0 | 16 | 15.28 ± 2.22* |
|  | 50.0 | 16 | 13.86 ± 2.16** |
| Compound V | 12.5 | 8 | 13.79 ± 2.14** |
|  | 25.0 | 8 | 13.75 ± 2.90** |
| Compound VI | 6.3 | 8 | 16.33 ± 3.87* |
|  | 12.5 | 8 | 15.39 ± 3.00* |
|  | 25.0 | 8 | 13.00 ± 1.50** |
| Compound VII | 6.3 | 8 | 18.00 ± 6.93 |
|  | 12.5 | 8 | 16.93 ± 4.47 |
|  | 25.0 | 8 | 11.82 ± 0.90** |
| Compound IV | 12.5 | 8 | 17.81 ± 3.78 |
|  | 25.0 | 8 | 14.42 ± 2.71** |
| Bicyclic Glycoside Derivatives of Pseudopterosin | | | |
| Compound VIII | 25.0 | 16 | 13.93 ± 2.59** |
|  | 50.0 | 16 | 12.07 ± 1.69** |
| Compound IX | 25.0 | 16 | 15.85 ± 2.51* |
|  | 50.0 | 16 | 14.04 ± 2.38** |
| Compound X | 50.0 | 6 | 10.64 ± 1.93** |

*Statistically significant, $p < 0.05$, Student's t-test, one-tailed
**Statistically significant, $p < 0.01$, Student's t-test, one-tailed

TABLE V

Analgesia Against Intraperitoneally Administered Phenylquinone

| Treatment | Dose (mg/kg) | No. Writhes | No. Animals | Mean Writhes per Animal | % Change Relative to Control |
|---|---|---|---|---|---|
| Vehicle | — | 83 | 9 | 9.2 |  |
| Compound IX | 25 | 68 | 10 | 6.8 | −26 |
| Compound II | 25 | 91 | 10 | 9.1 | −1 |
| Compound IV | 25 | 55 | 9 | 6.1 | −34 |
| Vehicle | — | 103 | 9 | 11.4 |  |
| Compound VII | 25 | 66 | 10 | 6.6 | −42 |
| Vehicle | — | 36 | 5 | 7.2 |  |
| Compound XIII | 25 | 31 | 4 | 7.8 | +8 |
| Compound V | 25 | 22 | 5 | 4.4 | −39 |
| Vehicle | — | 47 | 4 | 11.8 |  |
| Compound XI | 25 | 37 | 3 | 12.3 | +4 |
| Compound XII | 25 | 25 | 2 | 12.5 | +6 |

TABLE VI

Analgesic Activity of Compound III Against Intraperitoneally Administered Phenylquinone - Preliminary Dose Response Data

| Treatment | Dose mg/kg | N | Mean No. Writhes |
|---|---|---|---|
| Vehicle Control | — | 4 | 8.63 ± 0.62 |
| Compound III | 6.3 | 3 | 5.11 ± 0.21* |
| Compound III | 12.5 | 3 | 3.98 ± 0.64* |
| Compound III | 25.0 | 3 | 1.20 ± 0.75* |
| Compound III | 50.0 | 3 | 0 |

*Statistically significant difference, $p < .05$, Student's t-test

The vheicle or carrier for the compounds used in the inflammatory and analgesic assays was as follows; For the mouse ear inflammatory assay, the vehicle was acetone. Controls received 25 microliters of acetone. Test compounds were applied to the experimental animals in 25 microliter volumes. For the sperm motility and fertilized sea urchin egg assays, the compounds were dissolved in 10 microliters undenatured ethanol.

For the phenylquinone writhing assays, phenylquinone was administered at 2 mg per kg intraperitoneally in 5% ethanol-95% physiological saline. Test compound was administered subcutaneously in sesame oil at concentrations up to 5 mg per ml depending on the test compound dosage protocol. The highest dose was 50 mg per Kg. Control groups received sesame oil subcutaneously.

A summary of the results of the testing for antiinflammatory and analgesic activity is set forth in Table VII.

TABLE VII

Summary of Anti-inflammatory and Analgesic Activities of Pseudopterosin A and its Derivatives

| Compound No. | Anti-inflammatory Activity | Analgesic Activity |
|---|---|---|
| Pseudopterosin A Glycosides | | |
| I | Active | Active |
| II | Active | Inactive |
| III | Active | Active |
| IV | Active | Active |
| V | Active | Active |
| VI | Active | Not Tested |
| VII | Active | Active |
| Bicyclic Glycoside Derivatives of Pseudopterosin | | |
| VIII | Active | Active |
| IX | Active · | Active |
| X | Active | Not Tested |

Application of 50 microgram pseudopterosin A (Compound I) results in a 69% decrease in edema. The standard anti-inflammatory agent indomethacin, by comparison, produces only a 50% decrease in edema at the same dose. Pseudopterosin also totally inhibits cell division at doses as low as $7 \times 10^{-6}$M, and sperm motility at the standard test dose of 16 microgram/ml ($10^{-5}$m). Pseudopterosin also provides analgesia against chemically induced pain. The other exemplary synthetic and natural derivatives of pseudopterosin which were tested provided similar results.

Compound I was also evaluated in mice bearing P388 Leukemia as follows:

Compound I was administered to the mice as a solution by first dissolving it in N,N-dimethylacetamide, adding an equal volume of Cremophor EL and then 8 volumes of water. The drug concentration was such that the desired dose was delivered in a volume of 0.5 ml per mouse. Dilutions from the highest dose in a dose-response study were made by the addition of water so that organic component of the formulation decreased with dose reduction; the drug remained in solution.

$10^6$ P388 leukemia cells were implanted intraperitoneal in female $B6D2F_1$ mice which were randomized to treatment groups of six animals each. Treatment was initiated 24 hours after tumor implantation and was continued daily for five days (Cisplatin was administered on Days 1 and 5 for the Group 1 mice). Mice were weighted as groups on Days 1, 5 and 9 to provide an indication of drug toxicity. Mice were monitored for survival daily for 45 days, and the median day of death was determined compared to three groups of untreated controls to provide percent increase in lifespan (ILS). ILS values of greater than or equal to 40 percent represent actual reduction in tumor cell burden during the course of treatment and are taken as indications of biologically significant antitumor effect. The results of the testing is set forth in Table VIII.

As can be seen from Table VIII, Compound I demonstrated reproducible activity in mice bearing intraperitoneal P388 leukemia. At the highest dose tested in the two groups, Compound I prolonged lifespan by 82 percent and 65 percent. The dose of 24 mg/kg/day produced 82 percent increase in lifespan (ILS). A similar dose in the second group was ineffective (a prolongation of lifespan of greater than or equal to 40 percent represents biologically significant tumor cell kill on this treatment schedule) whereas significant activity was seen at 60 mg/kg/day. A daily dose in this range appears from the weight loss seen in this example and subsequent examples for the solid tumor models set forth below, to be the maximally tolerated dose of Compound I.

The toxicity of single intraperitoneal (ip) doses of Compound I in female $B6D2F_1$ mice were evaluated. Doses of up to 150 mg/kg produced no lethality but signs of CNS toxicity were evident at doses greater than or equal to 77 mg/kg. Symptoms included hypersensitivity to external stimuli and shivering.

Compound I was also evaluated for activity against solid tumors as follows:

One-half ml of a 10 percent (v:v) brei of tumor cells prepared from solid B16 melanoma or M5076 reticulum cell sarcoma was implanted ip in female $B6D2F_1$ mice which were randomized to treatment groups of 8 animals each. Treatment was initiated 24 hours after tumer inoculation and was continued daily for 10 days (cisplatin was administered q4Dx4 on Days 1, 5, 9 and 13). Mice were monitored daily for 60 days, and the median day of death was determined compared to three groups of untreated controls to provide percent increase in lifespan (ILS). ILS values of greater than or equal to 50 percent represent biologically significant antitumor effects. Cisplatin was curative in M5076 with 6/8 tumor-free survivors on Day 60 at the top dose level. The results of these tests are set forth in Table IX.

TABLE VIII

Evaluation of Compound I (Pseudopterosin A) Bearing ip P388 Leukemia

| Drug | Dose (mg/kg, ip, Days 1-5) | Weight Change (gm) Day 5 | Weight Change (gm) Day 9 | Median Survival Time (days) | Increase to Lifespan (%) |
|---|---|---|---|---|---|
| Group 1 | | | | | |
| Control | | +0.3 | +4.6 | 11 | |
| | | +0.2 | +6.1 | 11.5 | |
| | | +0.4 | +4.8 | 11.5 | |
| Cisplatin | 6 | −1.2 | −1.1 | 30.5 | 177 |
| (Positive Control) | 3 | +0.3 | +1.1 | 25 | 127 |
| Pseudopterosin A | 24 | +0.4 | −0.6 | 20 | 82 |
| | 12 | −2.6 | +1.3 | 16 | 45 |
| | 6 | +0.7 | +2.9 | 15 | 36 |
| | 3 | +0.4 | +4.2 | 14 | 27 |
| | 1.5 | +0.1 | +4.6 | 14 | 27 |
| Group 2 | | | | | |
| Control | | +2.2 | +4.7 | 10 | |
| | | +1.8 | +5.0 | 9.5 | |
| | | +1.8 | +4.8 | 10.5 | |
| Cisplatin | 2 | −2.5 | −0.9 | 30 | 200 |
| (Positive Control) | 1 | −0.2 | +0.1 | 17.5 | 75 |
| Pseudopterosin A | 60 | −3.2 | −0.5 | 16.5 | 65 |
| | 40 | −2.1 | +2.2 | 13 | 30 |
| | 26.7 | −0.7 | +3.4 | 12.5 | 25 |
| | 17.8 | 0 | +2.8 | 11.5 | 15 |
| | 11.9 | +0.7 | +2.5 | 11.5 | 15 |
| | 7.9 | +1.1 | +3.6 | 11 | 10 |

TABLE IX
Activity of Pseudopterosin A in Mice Bearing ip Solid Tumors

| Drug | Dose (mg/kg, ip, Days 1-5) | Weight Change (gm on Day 9) | Median Survival Time (days) | Increase to Lifespan (%) |
|---|---|---|---|---|
| ip M5076 Reticulum Cell Sarcoma | | | | |
| Control | | +1.1 | 21 | |
| | | +1.6 | 21 | 21 |
| | | +2.0 | 21 | |
| Cisplatin | 5 | −1.6 | >60 | >200 |
| (positive control) | 3 | +0.1 | 46.5 | 121 |
| Pseudopterosin A | 66.7 | −2.9 | 21.5 | 2 |
| | 40 | −1.1 | 20.5 | −2 |
| | 24 | +0.6 | 21 | 0 |
| | 14.4 | +0.2 | 21 | 0 |
| | 8.64 | +0.1 | 20.5 | −2 |
| ip B16 Melanoma | | | | |
| Control | | +1.2 | 20.5 | |
| | | +1.6 | 22.5 | 22 |
| | | +1.1 | 21.5 | |
| Cisplatin* | 6 | +0.5 | 39 | 77 |
| (positive control) | 3 | +1.6 | 30 | 36 |
| Pseudopterosin A | 50 | −0.4 | 21 | −4 |
| | 30 | +0.5 | 24.5 | 11 |
| | 18 | +0.9 | 21.5 | −2 |
| | 10.8 | +1.0 | 20.5 | −7 |
| | 6.48 | +1.2 | 21.5 | −2 |

The results shown in Table IX indicate that Compound I did not demonstrate significant antitumor activity against either the M5076 reticulum cell sarcoma or the B16 melanoma.

The above examples demonstrate that Compound I is effective in treating lymphoma type cancers, but has not yet been demonstrated to be effective, when used alone, against solid tumors such as sarcomas and melanomas which have been established in the host.

Compound I and the other related naturally occurring and synthetic pseudopterosin compounds are expected to be effective when used alone in treating lymphoma type cancers and also to be effective against other types of cancers, including solid tumors, when used alone or in combination with anti-cancer drugs in a chemotherapy program and treatment schedule.

Compound I was also tested for antiproliferative effects on tumor cells growing in tissue culture. For these tests, a highly metastatic subline (F10) of B16 melanoma was used and found that a continuous exposure of 42 uM Compound I inhibited proliferation by 50 percent. This demonstrates that Compound I has potency as a cytotoxic agent agaisnt proliferating cells.

Pseudopterosin compounds in accordance with the present invention are a combination of a ribose, arabinose or hexose sugar moiety and a diterpene moiety. Exemplary diterpene or aglycone moieties were tested for analgesic and anti-inflammatory activity in the same manner as compounds I-X. The aglycones which were tested were:

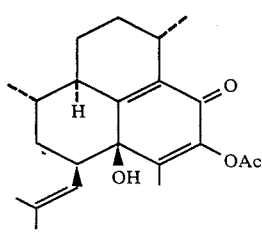

COMPOUND XI

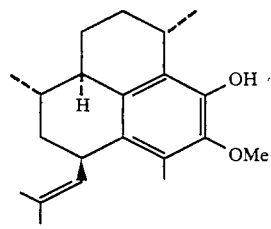

COMPOUND XII

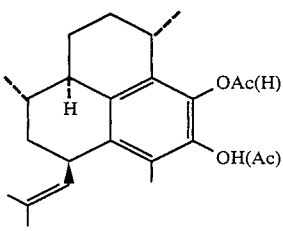

COMPOUND XIII

None of the three aglycones (XI–XIII) were found to have anti-inflammatory or analgesic activity. It is believed that the unique combination of the diterpene moiety and the sugar moiety in pseudopterosin and pseudopterosin derivative compounds is responsible for the biological activity of the compounds. The particular group ($R_1$–$R_6$) does not appear to be critical so long as the R groups are within those classes of hydrocarbon groups set forth in this specification. R groups having greater number of carbon atoms are preferred in many cases since they produce a compound having higher lipophilicity which provides improved membrane transport characteristics which are useful when the compounds are applied topically.

The following side effect of pseudopterosin A (Compound I) was observed. Doses of 12.5 mg/kg to 50 mg/kg, administered subcutaneously to mice (dissolved in sesame oil, 0.1 cc volume/10 gm body weight) produce central nervous system excitation, brief involuntary muscle contraction of the hind limbs resulting in lateral jumping movements, excessive preening of wound sites, and flushing of the tail and ears. These effects begin within a few minutes of administration and last up to one hour. Doses as low as 3 mg/kg produce slight to moderate central nervous system excitation.

Doses up to 50 mg/kg administered intraperitoneally to mice have no effect. At 100 mg/kg and above, pseudopterosin produces mild excitation and writhing in some animals, with return to normal activity within 30 minutes. Mortality at 100 mg/kg=2/10 on day after administration, at 200 mg/kg=2/4 also on day after administration.

The novel pseudopterosin compounds in accordance with the present invention are useful in the treatment of rheumatoid arthritis, osteoarthritis, rheumatic carditis, collagen and/or auto-immune diseases such as myasthenia gravis, allergic diseases, bronchial asthma and ocular and skin inflammatory diseases such as poison ivy. The compounds are also useful in treating proliferative diseases such a psoriasis. The compounds are useful in treating other skin diseases such as richen planus and pemphigus.

The usefulness of these compounds in treating leukemia type cancers has been demonstrated. Leukemia type cancers such as acute lymphoblastic leukemia, acute myeloblastic leukemia, acute monoblastic leukemia, chronic lymphocytic leukemia and chronic granulocytic leukemia can be treated. Further, the compounds are expected to be useful against other types of cancers when used along or in combination with other anti-cancer drugs.

The compounds are also useful as adjuvant therapy associated with organ and tissue transplants and any neurological disease involving metabolism of nervous tissue phospholipid such as multiple sclerosis. Because of their selective antagonism of chemical irritationn (i.e., PMA inflammation) pseudopterosin compounds can be useful in the treatment of insect bites, bee or wasp stingns or any venom in which a major constituent is the enzyme phospholipase $A_2$. The compounds are potent nonnarcotic analgesics and may be used to alleviate pain resulting from traumatic injury or acute progressive disease, such as post operative pain, burns, or other conditions involving a coincident inflammation.

The pseudopterosin compounds in accordance with the present invention are administered to mammals including humans in an effective amount on the order of 10 to 50 mg per day per kilogram of body weight. The drug may be administered orally, parenterally, topically or by other standard administration routes. The dosage form may be by tablet containing normal acceptable additives, excipients, etc. The parenteral form contains typical aqueous intravenous solution ingredients such as propylene glycol and physiological saline or other suitable lipid solubilizing carrier.

Comparative studies of Compounds I, IV, XV and a compound which is a derivative of Pseudopterosin A wherein $R_1=CH_3$; $R_2$, $R_3$, $R_4$ and $R_5$=hydrogen and $R_6$=2-methyl-1-propene (Compound XX) were also conducted.

Phenyl-p-benzoquinone Assay for Analgesia

Compounds I, IV and XV were dissolved in 10% ethanol/sesame oil. Intraperitoneal injections of 0.1 ml/10gm mouse weight were given over the dose range 1.56 mg/kg to 300 mg/kg 30 minutes prior to phenyl-p-benzoquinone (PQ). Each mouse received 0.1 ml/10gm mouse wt of a 0.2 mg/ml PQ solution intraperitoneally. Writhes were counted for a 10 minute interval, following a 10 minute waiting period. $ED_{50}$ is defined as the dose that produced a 50% inhibition of writhing. $ED_{50}$ values were estimated by the method of Litchfield and Wilcoxon.

Anti-Inflammatory Assay (systemic administration)

2 ug PMA was applied in 25 ul of acetone to the inner surface of the left ear of male Swiss Webster mice (4 to 6 weeks old), the right ear is treated with acetone only. Compounds I, XV and XX) injections of 0.1 ml/10gm mouse weight were given over the dose range 3.13 mg/kg to 200 mg/kg one hour before PMA application. 200 minutes after PMA treatment, the mice were killed by cervical dislocation and both ears were cut off, punched with a #4 cork borer and weighed. The swelling induced by PMA was calculated as the increase in the weight of the left ear minus the right ear. The percent inhibition of edema was calculated as control-drug/control×100. $ED_{50}$ is defined as the dose that produced a 50% inhibition of inflammation. $ED_{50}$ values were estimated by the method of Litchfield and Wilcoxon.

Anti-Inflammatory (topical administration)

2 ug PMA was applied in 25 ul of acetone of the inner surface of the left ear, the right ear is treated with solvent only. Compounds I, IV, XV and XX were incorporated in the PMA solution and applied to the left ear in doses of 6.25 ug to 100 ug. 200 minutes after PMA treatment, the mice were killed by cervical dislocation and both ears were cut off, punched with a #4 cork borer and weighed. The swelling induced by PMA was calculated as the mean increase in the weight of the left ear minus the right ear. The pecent inhibition of edema was calculated as control-drug/control×100. $ED_{50}$ is defined as the dose that produced a 50% inhibition of inflammation. $ED_{50}$ values were estimated by the method of Litchfield and Wilcoxon.

The results of the above three test comparisons are set forth in Tables X, XI and XII.

TABLE X

| | Assay for Analgesia | | | | |
| | % Inhibition | | | | % Inhibition |
| Dose (mg/kg) | Compound IV | Compound XV (s.q.) | Compound XV (i.p.) | Dose (mg/kg) | Compound I (s.q.) |
| --- | --- | --- | --- | --- | --- |
| 300 | 90% | | | 20 | 96% |
| 200 | 72% | | | 10 | 73% |
| 100 | 66% | | | 7.5 | 79% |
| 50 | 58% | | 90 | 5.0 | 38% |
| 25 | 54% | 57% | 65% | 3.5 | 46% |
| 12.5 | 44% | 49% | 62% | 2.0 | 29% |
| 6.2 | 39% | 39% | 42% | | |
| 3.1 | 30% | 33% | | | |
| 1.6 | 11% | | | | |

Compound I - $ED_{50}$ = 4.22 mg/kg*
Compound XV - $ED_{50}$ = 14.3 mg/kg*
Compound IV - $ED_{50}$ = 21.5 mg/kg*
*(n = 10 mice/dose)

TABLE XI

| | Anti-Inflammatory Assay (systemic administration) | | | |
| | % Inhibition | | | |
| Dose (mg/kg) | Compound XV | Compound I | Compound XX | Compound IV |
| --- | --- | --- | --- | --- |
| 300 | | | 98.5% | |
| 200 | | | 65.9% | 41.0% |
| 100 | | 90.4% | 34.8% | 44.7% |
| 50 | 97.3% | 46.5% | 12.5% | 38.5% |
| 25 | 75.0% | 43.8% | 0 | 27.6% |
| 12.5 | 36.5% | 24.4% | 0 | 22.3% |
| 6.25 | 16.1% | 0 | 0 | — |

TABLE XI-continued

Anti-Inflammatory Assay (systemic administration)

| Dose (mg/kg) | % Inhibition | | | |
|---|---|---|---|---|
| | Compound XV | Compound I | Compound XX | Compound IV |
| 3.12 | 0 | | | 8.5% |

Compound XV - ED$_{50}$ = 14.4 mg/kg*
Compound I - ED$_{50}$ = 31.8 mg/kg*
Compound XX - ED$_{50}$ = 131.2 mg/kg*
Compound IV - ED$_{50}$ = Maximum inhibition <50%
*(n = 10 mice/dose)

TABLE XII

Anti-Inflammatory Assay (topical administration)

| Dose (ug/ear) | % Inhibition | | |
|---|---|---|---|
| | Compound XV | Compound I | Compound XX |
| 100 | 95.3 | | |
| 50 | 78.6 | 96.0 | 78.7 |
| 25 | 27.9 | 89.5 | 78.2 |
| 12.5 | 0 | 78.3 | 44.2 |
| 6.25 | | 28.8 | 11.3 |

Compound I (ED$_{50}$) = 8.3 ug/ear*
Compound XX (ED$_{50}$) = 16.7 ug/ear*
Compound XV (ED$_{50}$) = 38.0 ug/ear*
*(n = 10 mice/dose)

In the comparative tests, the CNS activity previously mentioned for Compound I was not present with Compounds IV, XV or XX. After injection of these three compounds, there were no symptoms of excitation, vocalization or aggressive-defensive stances. All mice that were treated with Compounds IV and XX survived to days post-treatment, there was no deterioration with time and no latent toxicity. Animals treated with Compound XV exhibited a much decreased toxicity, with the maximum mortality below 50%. There was no toxicity at doses up to 100 mg/kg, 4/10 mice at 200 mg/kg and 1/5 mice at 300 mg/kg died within 5 days. All animals that survived 5 days were equal to the control mice in appearance. During the anti-inflammatory assay the animals receiving Compound I exhibited the CNS stimulation described previously.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A compound having the structure:

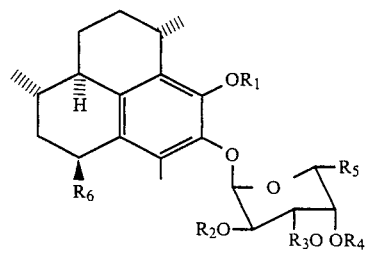

wherein $R_1$, $R_2$, $R_3$ and $R_4$ are hydrogen or an acyl group having from 1 to 6 carbon atoms, $R_5$ is hydrogen, $CH_3$ or $CH_2OH$, and $R_6$ is a hydrocarbon having from 1 to 10 carbon atoms.

2. A compound according to claim 1 wherein $R_1$, $R_2$, $R_3$, $R_4$ and $R_5$ are hydrogen and $R_6$ is 2-methyl-1-propene.

3. A compound according to claim 2 wherein $R_6$ is 2-methyl-1-propene oxide.

4. A compound according to claim 1 wherein $R_1$, $R_2$, $R_3$ and $R_4$ are acetate.

5. A compound according to claim 1 wherein $R_1$, $R_2$, $R_3$ and $R_4$ are hydrogen and $R_5$ is $CH_3$.

6. A compound according to claim 5 wherein $R_6$ is 2-methyl-1-propene.

7. A method for treating mammals suffering from pain to reduce pain which comprises:
administering to said mammal a pain reducing effective amount of a composition consisting essentially of seco analogs of compounds having the structure:

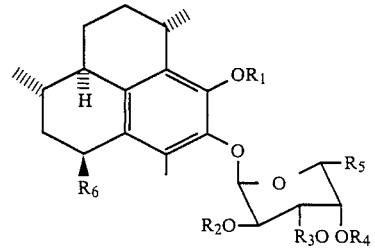

wherein $R_1$, $R_2$, $R_3$ and $R_4$ are hydrogen or an acyl group having from 1 to 6 carbon atoms; $R_5$ is hydrogen or $CH_2OH$ and $R_6$ is a hydrocarbon having from 1 to 10 carbon atoms; and a pharmaceutically acceptable carrier compound therefor.

8. A method for treating mammals having inflamed tissue to reduce inflammation which comprises:
administering to said mammal an inflammation reducing effective amount of a composition consisting essentially of seco analogs of compounds having the structure:

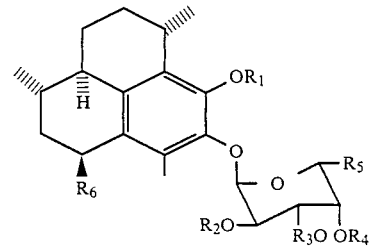

wherein $R_1$, $R_2$, $R_3$ and $R_4$ are hydrogen or an acyl group having from 1 to 6 carbon atoms; $R_5$ is hydrogen, $CH_3$ or $CH_2OH$ and $R_6$ is a hydrocarbon having from 1 to 10 carbon atoms; and a pharmaceutically acceptable carrier compound therefor.

9. A method for treating mammals having inflamed tissue to reduce inflammation according to claim 8 wherein $R_1$, $R_2$, $R_3$ and $R_4$ are hydrogen, $R_5$ is $CH_3$ and $R_6$ is 2-methyl-1-propene.

10. A method for treating mammals suffering from pain to reduce pain according to claim 7 wherein $R_1$, $R_2$, $R_3$ and $R_4$ are hydrogen, $R_5$ is $CH_3$ and $R_6$ is 2-methyl-1-propene.

* * * * *